United States Patent
Vogel

[11] Patent Number: 6,146,137
[45] Date of Patent: Nov. 14, 2000

[54] CONTAMINATION PREVENTION DEVICE FOR ULTRA HIGH SPEED DENTAL TYPE HANDPIECES

[76] Inventor: William Charles Vogel, 18500 E. Aschoff, Zigzag, Oreg. 97049-9707

[21] Appl. No.: 09/196,642

[22] Filed: Nov. 19, 1998

[51] Int. Cl.[7] .................................................. A61C 1/05
[52] U.S. Cl. ........................................... 433/132; 415/904
[58] Field of Search ................................... 433/132, 120, 433/131, 133; 415/904

[56] References Cited

U.S. PATENT DOCUMENTS

| | | | |
|---|---|---|---|
| 3,175,293 | 3/1965 | Borden | 433/132 |
| 3,567,330 | 3/1971 | Apelskog et al. | 433/132 |
| 3,708,240 | 1/1973 | Theis, Jr. et al. | 433/132 |
| 3,775,851 | 12/1973 | Flatland | 433/132 |
| 3,865,505 | 2/1975 | Flatland . | |
| 4,470,813 | 9/1984 | Thornburn | 433/132 |
| 4,786,251 | 11/1988 | Ruegsegger | 433/132 |
| 5,340,312 | 8/1994 | Murase | 433/132 |
| 5,407,352 | 4/1995 | Kawata | 433/132 |
| 5,464,350 | 11/1995 | Bierbaum | 433/114 |
| 5,476,380 | 12/1995 | Rosenstatter | 433/100 |
| 5,507,642 | 4/1996 | Wohlgemuth | 433/132 |
| 5,676,542 | 10/1997 | Lingenhöle et al. | 433/115 |
| 5,782,634 | 7/1998 | Lingenhöle et al. | 433/132 |

*Primary Examiner*—Ralph A. Lewis
*Attorney, Agent, or Firm*—Patent & Trademark Services; Thomas Zack; Joseph H. McGlynn

[57] ABSTRACT

A gas turbine operated handpiece instrument having a spin able front shaft mounted bur that is operated by pressurized gas or air. Two embodiments are disclosed. In one a flexible rubber like PVC one-way pinch valve is mounted on an exterior gas exhaust stack of the instrument's body housing. This embodiment allows for the internal lubrication of the turbine parts by compressing the valve sides towards each other and then spraying a lubricate into the housing through the opened valve. In another embodiment, a metallic one-way ball valve is mounted within an extension to the housing and this design is more suitable for dental bur offset instruments. In both designs, the turbine has impellers located within the hollow body of the instrument. The purpose of the one-way valves in both embodiments is to prevent contaminates from being sucked back into the housing as the gas turbine is being shut down during its complete operating range. A rear mounted hand operated plunger is connected to a plunger shaft to permit the ejection of the aligned bur's shaft when a bur change is desired.

2 Claims, 2 Drawing Sheets

FIG. 4
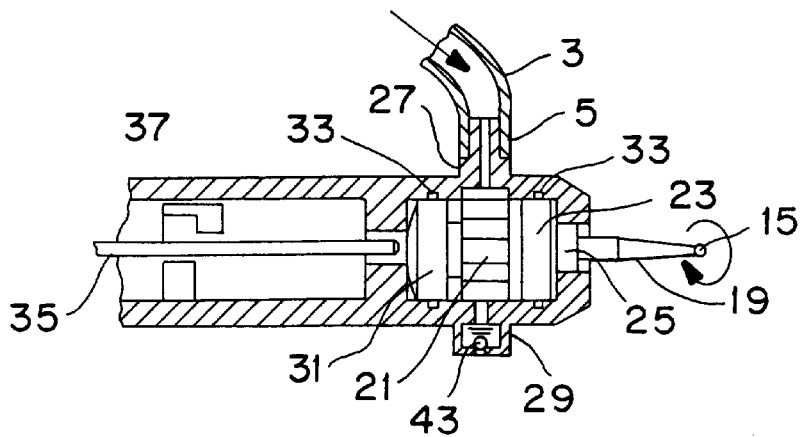
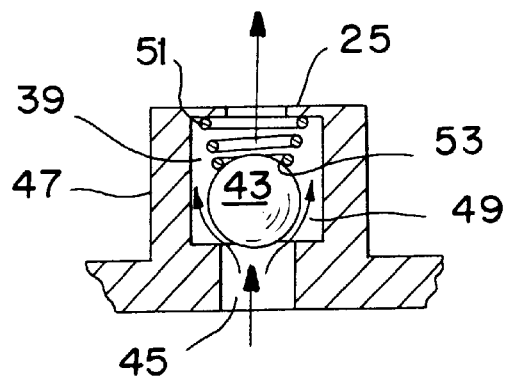
FIG. 5(a)
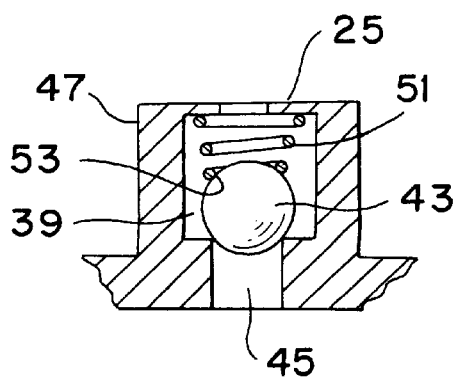
FIG. 5(b)

CONTAMINATION PREVENTION DEVICE FOR ULTRA HIGH SPEED DENTAL TYPE HANDPIECES

BACKGROUND OF THE INVENTION

Ultra high speed dental type handpiece instruments are conventionally configured in two major configurations. In one configuration the bur is aligned in a straight line with the dental instrument's handle. This configuration is used in dental laboratories for shaping anatomy and can also be used by wood carvers, glass engravers and other arts and craft users. It is not used in the oral cavity.

In the second configuration, used by dentists within the oral cavity, called a contra angle handpiece, the cutting bur is angled sharply with respect to the handle. This angled mounting of the bur is necessary for the user to reach the top and bottom of a tooth structure. Other features the second configurations may have over those in the first configuration include fiber optics, and chip air and water lines to cool the tooth.

The present invention discloses a new handpiece design which is similar to the first configuration, or laboratory style instrument, but differs by the way a turbine which is powered by the routing of input and exhaust gases. The inputted air is directly supplied to the front of the instrument near its bur head, rather than through or near the rear handle. In addition, the exhaust gas is not routed through the handle. By using a short length of PVC (polyvinyl chloride) tubing pinched closed at one end and mounted on the front end of the instrument near the bur, several advantages are achieved.

One of the advantages is lubrication. In conventional designs lubrication is fed to the turbine by removing the input tubing from the handpiece and applying oil into the tubing resulting in most of the lubrication blowing out, without touching the internal bearings. In the present invention,. an aerosol lubricator, similar to WD40 ™ is used by squeezing an exhaust port with the fingers to make the tubing round and then inserting the aerosol tip into the exhaust stack while pressing the plunger once. This applies a metered amount of lubrication directly into the turbine bearings, saturating them. Using a pinched end for the exhaust stack also has the added advantage of preventing dirt from entering the turbine housing should the handpiece be laid down in dirt.

Still another advantage of using a pinched exhaust stack relates to an inherent problem in ultra high speed dental type instruments. As compressed gas.is used to power the instrument and there is positive air pressure existing in the instrument, there is no chance that dirt will enter the turbine housing. However, when the compressed gas supply is removed, the handpiece turbine continues to spin for several seconds as a result of momentum. During this time the spinning action becomes a vacuum pump and pulls contaminated air up the spindle, directly into the front bearing. For this reason dental handpieces need to be autoclaved to kill any biological matter that might have entered the turbine housing during its shut down operation. In the present invention, the pinched exhaust stack tubing causes the drive air pressure to decline slowly as it also closes the exhaust port to prevent the described vacuum pump phenomenon called "suck up".

Details of the construction and operation of the present invention are described hereafter.

DESCRIPTION OF THE PRIOR ART

Air operated hand held dental instruments that are used to cut, grind, carve or engrave are known. For example, in the Murase invention (U.S. Pat. No. 5,340,312) an anti-contamination type elongated hand piece of a dental instrument is disclosed having an air turbine driven by compressed air. To prevent Karman's vortex street in the instrument, the inventor designed a unique rectilinear means formed by helical ridges or slots in the inner surface of air holes.

The Rosenstatter patent (U.S. Pat. No. 5,476,380) discloses a dental handpiece with a selectively detachable tool holder that can be driven by either a mechanical structure or an air turbine.

In U.S. Pat. No. 5,507,642 to Wohlgemuth a dental turbine drive with an arrangement to prevent suctioning of particles after deactivation of the drive air into the return air is disclosed.

In the Lingenhole et al. reference (U.S. Pat. No. 5,676,542) the dental instrument described has a turbine driven straight, or angled, headpiece wherein roller bearing are sealed against contamination with a blocking ring.

The present invention relates to a turbine operated hand held instrument with an air pressure regulator to maintain a constant back pressure to prevent contamination from entering the turbine housing all as more fully set forth in this specification.

SUMMARY OF THE INVENTION

This invention relates to a dental handpiece instrument having a spinable front bur that is operated by an air driven turbine within the instrument. A pressure regulator is used to prevent outside contamination from entering the instrument during all of its complete operating range.

It is the primary object of the present invention to provide for an improved air turbine driven handpiece instrument having a pressure regulator to prevent contamination from entering the handpiece's housing.

Another object is to provide for such a handpiece used in the dental art wherein the pressure regulator maintains a constant back pressure within the housing for the turbine.

These and other objects and advantages of the present invention will become apparent to readers from a consideration of the ensuing description and the accompanying drawings.

BRIEF DESCRIPTION OF THE DRAWINGS

FIG. 4 is a side cross sectional view of a different exhaust type of valve used in place of the FIG. 2 device when the handpiece is not lubricated through its exhaust port.

FIGS. 5(a) and (b) are enlarged cross sectional views of the ball type of exhaust valve used in the FIG. 4 embodiment.

DESCRIPTION OF THE PREFERRED EMBODIMENT

Figure 1:
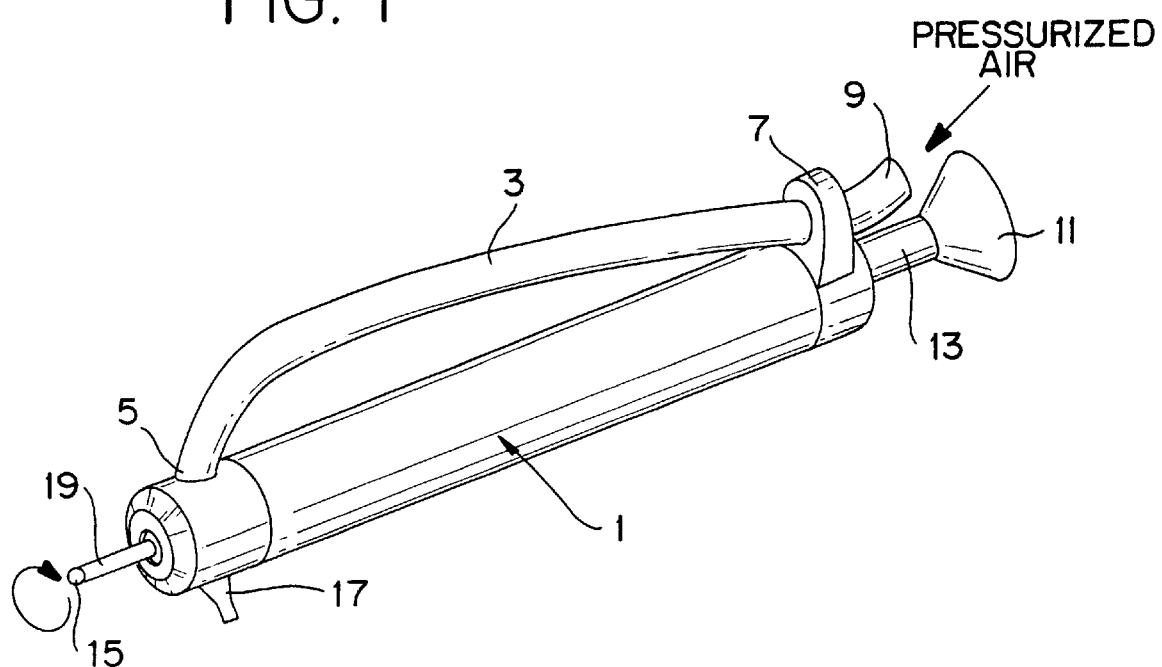
FIG. 1 is a perspective view of the invention's preferred embodiment.

FIG. 1 is a perspective view of the invention's preferred embodiment. The hollow, cylindrically shaped plastic housing or body member 1 has a gas inlet with a gas or air input tube 3 mounted on an extension with an internal passageway fixed to the body 1. At the body's front end, pressured gas, such as ambient air, is inputted to the interior of the hollow body at the inlet passageway or port 5. A rear plastic loop 7 molded at its ends is mounted into the upper rear surface of the body 1 and acts to retain the rear of tube member 3 in place on the body 1.

A remote source of pressurized gas or air (not shown) is connected by tubing to the opened, rear end 9 to supply pressurized gas, ranging generally from 0 to up to 55 pounds per square inch (psi), to the hollow interior of the body 1. A reciprocable finger operated rear end plunger 11 is associated with the rod 13, and the plunger extends from the external rear of the housing into the hollow interior of the body 1. At the front end of the body a spinable bur end 15 is mounted on the rotatable supporting rod 19. By pressing forward on the rear plunger end 11 the extension to rod 19, that is within the body 1, can be ejected when it is desired to replace the rod and its bur end 15 and then permit a new rod and bur end to be inserted in its place.

On a body extension, with an internal passageway at the lower front side of the body 1, the outer valve 17 forms parts of the interior exhaust gas stack housing. The valve 17 is made of a flexible PVC material that is biased such that under normal conditions its internal gas passageway is pinched closed to the passage of gas through the valve to the outside of the housing. When sufficient internal gas pressure is developed, about 3 to 5 psi, within the housing, however, a normally closed passageway within the valve opens to allow for the passage of gas from the housing to its exterior.

Thus, depending on applied gas pressure, the pinch valve acts as a one-way check valve to either prevent the entry of external gas, and matter, into the housing or to allow gas and matter to exit from the housing 1. Within the confines of the housing or body 1 is a gas or air operated'turbine that is used to rotate the rod 19 and its front bur end 15. This rotation is powered by pressurized gas supplied via tube 3 to the turbine. The bur end rotates in unison with the turbine's impeller (see FIG. 2) and is mounted within the hollow body 1. As compressed gas is injected over these internal impeller blades of the turbine, the bur's shaft spins at speeds approaching 400,000 revolutions per minute (rpm). There is very little torque as the spinning of the bur shaft is based on the principle of high "angular velocity". Spent air exits from the turbine and the body 1 via a gas outlet in the body of the end of the passageway opening in the pinch valve exhaust stack 17.

Figure 2:
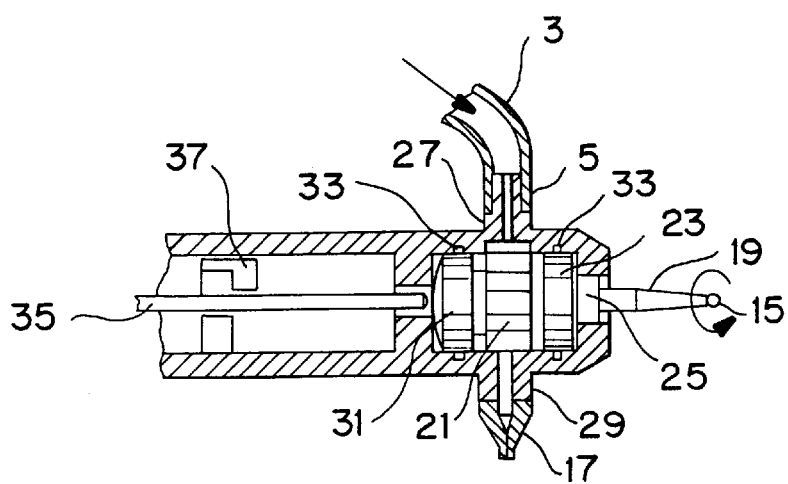
FIG. 2 is a cross sectional view of the front portion of the FIG. 1 instrument with no supply air.

FIG. 2 is a reversed cross sectional view of the front portion of FIG. 1. In this view the PVC one-way pinch valve 17 for the lower gas exhaust stack is shown in a closed position. As pressurized gas enters the interior of hollow body 1 through the inlet gas opening 5 connected to tubing 3 (see arrow), the gas impinges upon the internal molded plastic turbine impeller 21 which rotates with the front bearing 23 and the front turbine spindle 25. There is a slight exterior side housing extension tubular member 27 with an external stepped diameter molded around the center input opening 5 into the body to permit the opened end of tubing 3 to fit around the housing extension and to form a tight fit around the body gas inlet opening. On the lower front end of the body 1 there is another molded exit stack exhaust extension with an internal passageway opening 29.

Figure 3A:
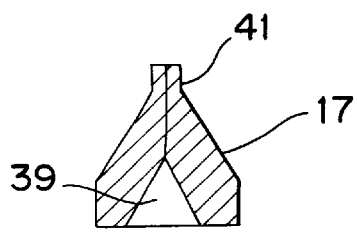
FIGS. 3(a) and (b) are cross sectional views of the pinched tube exhaust valve used in FIG. 2 when closed (FIG. 3(a)) and opened (FIG. 3(b)).

This outlet extension passageway communicates with the exterior passageway in the pinch one way check valve 17, shown in it closed and opened positions in FIGS. 3(a) and (b), respectively. To the front and rear of the turbine impellers 21, and mounted on the interior portion of shaft 19, are the two disk shaped bearing elements 23 and 31, respectively. These two shaft mounted bearing elements 23 and 31 rotate with the shaft 19 and its impeller 21 as pressurized gas (air) impinges upon the impeller's out blade surfaces to rotate the shaft. Several turbine retaining protrusions 33, molded into the interior hollow surface of the body 1, prevent the turbine assembly elements 23 and 31 from moving to the front or rear of the body as the centrally mounted plunger shaft 35 moves in the body 1.

The front end of plunger shaft 35 is shown in a straight line alignment with, but not touching, the center rear portion of impeller turbine assembly disk shaped element 31. Interior shaft guides and spring stop 37 are formed with a center through hole molded into the interior of the body 1 and acts to position the plunger's shaft 35 and insure the shaft's front end will point to the center of element 31. Centered on the rear end element 31 is front bur shaft 19. When the rear exterior plunger handle 11 is pressed forward it forces the element 35 into engagement with the rear end of bur shaft 19, pushing out shaft 19 and cutting bur end 15. When this reciprocable action takes place, only the bur's center support shaft 19 and bur end 15 are ejected while the other turbine assembly elements remain in place.

Figure 3B:
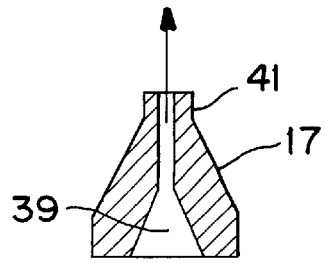

FIG. 3(a) is a cross sectional view of the pinch valve valve 17 when in its normally closed position with the turbine not operating. The flexible PVC material making up the valve 17 is normally compressed such that the front end 41 of the internal slit like passageway 39 is normally closed. As gas pressure builds up within the body 1, the valve's internal passageway is spread apart and its front 41 is forced opened as shown in FIG. 3(b), permitting the free flow of gas from the body 1. If one desires to lubricate the internal turbine component members within housing body 1, the opening 41 may be forced opened from outside the body 1 by compressing the two sides of the normally closed slit passageway of valve 17 inwardly towards each other with one's fingers. While the valve is in this opened state, a user then sprays a lubricating aerosol oil within the body 1 through the passageway openings 29 of the exhaust stack and its mounted valve as the pinch valve 17 remains in place on the housing. Thus, the normally closed pinch valve may be opened either by sufficient internal gas pressure or by applying an external compression pressure to its opposite sides outer surface.

FIG. 4 is essentially the same as the FIG. 2 embodiment, except that a metallic one-way check ball valve 43 is used in place of the PVC pinch valve 17. The body, turbine and other parts are metallic to allow their use without melting in a heated autoclave. This one-way ball valve 43 resides within the exit passageway 29 formed within a side housing extension 47 molded or cast into the exhaust air passage way of dental opatory handpieces. An inner reduced diameter passageway 45 in this extension 47 has a diameter less than that of the ball valve 43 and is used to retain the ball valve in place within the extension. Within the ball valve's retaining cavity 49 is a coil spring 51 that bears against the upper portion 53 of the ball valve 43. When pressurized air is exhausted, after impinging upon the impellers 21, if it has sufficient pressure, it can displace the ball valve 43 (see FIG. 5 (a)) from its normally spring biased seated position (see FIG. 5(b)). When displaced from its seated position by internal gas pressure working against the action of the bearing spring 51, there is a flow of gas around the displaced ball valve and out of the exit hole 29. The arrows indicate the direction of displacement of the ball valve 43.

As previously mentioned, since compressed gas is used to power the instrument when there is a positive air pressure existing within the instrument there is no chance that air-carried-dirt will enter the turbine housing 1. Once, the compressed gas supply is removed, however, the handpiece turbine continues to spin for several seconds as a result of momentum. During this short time frame the spinning action becomes a vacuum pump and pulls contaminated external air into the outlet opening and up the spindle directly into the front bearing. To prevent this vacuum pump action from taking place, a one-way valve, whether the pinch valve of FIGS. 1–2 or the ball valve of FIGS. 4–5, is used. These valves prevents dirt and other undesired contaminants external of the housing from being sucked into the housing as the turbine is shut off. The flexible external pinch valve has the added benefit of allowing lubrication to be applied to the internal turbine workings and this embodiment would be more useful in straight line bur instruments used for shaping anatomy, polishing porcelain and metal, engraving and general carving purposes. The ball valve embodiment would find greater applicability if offset from the handle (about 60 degree) bur cutting dental instruments used in the oral cavity since it is made of metal and therefore more reliable and more able to stand the heat of an autoclave unit. The material used for the tubing in the pinch valve would more likely melt in the heat of the autoclave unit.

Clearly, the basic principles used in the present invention need not be restricted to dental instruments. Any instrument having the elements as claimed are included within the scope of the subject matter covered.

The plastic injection molding process can be used to make the body member 1, its internal shaft and bearing retaining members, its external loop 7 and the outlet molded two body side inlet and outlet extensions as a single molded unit. Injection molding is a plastic molding process whereby heat softened plastic material is forced under very high pressure into a metal cavity mold, usually aluminum or steel, which is relatively cool. The inside cavity of the mold is comprised of two or more halves, and is the same desired shape as the product to be formed (in this case the body 1). High pressure hydraulics are used to keep the mold components together during the actual injection phase of the molding process. The injected plastic is allowed to cool and harden in the mold. The hydraulics holding the multiple component mold cavity together are released, the mold halves are separated and the solid formed plastic item is removed. Injection molding can be a highly automated process and is capable of producing extremely detailed parts at a very cost effective price. The process should be invaluable in producing this invention's handpiece cost effectively.

Although the preferred embodiment of the present invention and the method of using the same has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A handpieces instrument comprising:

a hollow body having a front end and a rear end, said body having a gas inlet port and a gas outlet port, said gas inlet port and said gas outlet port being mounted near the front end of the hollow body, said gas inlet port being connected to a conduit to provide a source of pressurized gas from a remote source;

said gas outlet port having a one way valve associated with said port to normally prevent the flow of gas into said hollow body and to permit the flow of gas from the hollow body when there is sufficient internal gas pressure within the body at the gas outlet port;

said one way valve associated with said gas outlet port being a flexible pinch valve having a gas passageway normally closed under atmospheric pressure and mounted external to said hollow body;

a gas driven turbine assembly mounted within said hollow body and in gaseous communication with said gas inlet port and said gas outlet port;

said turbine assembly having surface impellers and a center shaft with a length that is rotatable in unison with the surface impellers;

said impeller being rotatable when sufficient pressurized gas from a remote source impinges upon said impeller through said gas inlet port; and a front mounted bur end with a length, said bur end being mounted in generally straight axial alignment with the length of said center shaft of the turbine assembly and movable with said turbine assembly's center shaft.

2. The handpiece instrument as claimed in claim 1, wherein said pinch valve may be opened by hand to apply a lubricate to the exterior of said housing from outside housing by pressing said valve sides towards each other.

* * * * *